(12) United States Patent
Widdowson

(10) Patent No.: US 6,218,539 B1
(45) Date of Patent: Apr. 17, 2001

(54) IL-8 RECEPTOR ANTAGONISTS

(75) Inventor: Katherine L. Widdowson, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/202,568

(22) PCT Filed: Jun. 24, 1997

(86) PCT No.: PCT/US97/10906

§ 371 Date: May 10, 1999

§ 102(e) Date: May 10, 1999

(87) PCT Pub. No.: WO97/49400

PCT Pub. Date: Dec. 31, 1997

Related U.S. Application Data

(60) Provisional application No. 60/020,656, filed on Jun. 27, 1996.

(51) Int. Cl.[7] ........................ C07D 213/00; C07D 213/46
(52) U.S. Cl. ........................ 546/1; 546/304; 546/329; 546/340
(58) Field of Search ............................... 546/1, 304, 329, 546/340

(56) References Cited

U.S. PATENT DOCUMENTS

| | | | |
|---|---|---|---|
| 3,404,152 | 10/1968 | Thiele et al. | 546/105 |
| 4,001,256 | 1/1977 | Callahan et al. | 260/295 |
| 4,775,757 | * 10/1988 | Kannojia et al. | 544/362 |
| 5,328,922 | 7/1994 | Forbes et al. | 514/339 |

FOREIGN PATENT DOCUMENTS

| | | |
|---|---|---|
| 9422807 | * 10/1994 | (WO) . |
| WO97/49286 | 6/1997 | (WO) . |
| WO97/49399 | 6/1997 | (WO) . |
| WO97/49680 | 6/1997 | (WO) . |
| WO98/05317 | 8/1997 | (WO) . |
| WO98/05328 | 8/1997 | (WO) . |
| WO98/05329 | 8/1997 | (WO) . |
| WO98/06262 | 8/1997 | (WO) . |
| WO98/06397 | 8/1997 | (WO) . |
| WO98/06398 | 8/1997 | (WO) . |
| WO98/06399 | 8/1997 | (WO) . |
| WO98/32439 | 1/1998 | (WO) . |

OTHER PUBLICATIONS

Howard et al., "Chemokines: progress toward identifying molecular targets for therapeutic agents". Tibtech, Feb. 1996, vol. 14, pp. 46–51. Chem. Abstracts, 122:80891.
Synthesis (3), pp. 331–, 1985.
Reich, et al. J. Med. Chem. 32, pp. 2474–2485, 1989.
Sarkis, et al. J. Heterocyclic Chem., 22, pp. 137–140, 1985.
Kubota, et al. Chem. Pharm. Bull. 33(2), pp. 662–666, 1985.
Houghton, et al. J. Chem. Soc. Perkin Trans. 1,(7) pp 1471–1479, 1985.
Mayfield, et al. J. Med. Chem. (30) pp. 1595–1598, 1987.
Hull et al. J. Chem. Soc. Perkins Part I. No. 12, pp. 3037–3041, 1979.
Ser. No. 09/111,663, Widdowson, et al., filed Jul. 8, 1998.

* cited by examiner

*Primary Examiner*—Mukund J. Shah
*Assistant Examiner*—Sudhaker B. Patel
(74) *Attorney, Agent, or Firm*—Soma G. Simon; Dara L. Dinner; Charles M. Kinzig

(57) ABSTRACT

The present invention relates to the use of phenyl ureas in the treatment of disease states mediated by the chemokine, Interleukin-8 (IL-8).

16 Claims, No Drawings

IL-8 RECEPTOR ANTAGONISTS

This application is the §371 national stage entry of PCT/US97/10906, filed Jun. 24 1997 which claims the benefit of provisional application U.S. Ser. No. 60/020,656, filed Jun. 27, 1996.

FIELD OF THE INVENTION

This invention relates to a novel group of phenyl urea compounds, processes for the preparation thereof, the use thereof in treating IL-8, GROα, GROβ, GROγ, NAP-2 and ENA-78 mediated diseases and pharmaceutical compositions for use in such therapy.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al, *J. Clin. Invest.* 84, 1045 (1989); J. Schroder et al, *J. Immunol.* 139, 3474 (1987) and *J. Immunol.* 144, 2223 (1990); Strieter, et al, *Science* 243, 1467 (1989) and *J. Biol. Chem.* 264, 10621 (1989); Cassatella et al, *J. Immunol.* 148, 3216 (1992).

Groα, GROβ, GROγ and NAP-2 also belong to the chemokine α family. Like IL-8 these chemokines have also been referred to by different names. For instance GROα, β, γ have been referred to as MGSAα, β and γ respectively (Melanoma Growth Stimulating Activity), see Richmond et al, J. Cell Physiology 129, 375 (1986) and Chang et al, *J. Immunol* 148, 451 (1992). All of the chemokines of the a-family which possess the ELR motif directly preceding the CXC motif bind to the IL-8 B receptor.

IL-8, GROα, GROβ, GROγ, NAP-2 and ENA-78 stimulate a number of functions in vitro. They have all been shown to have chemoattractant properties for neutrophils, while IL-8 and GROα have demonstrated T-lymphocytes, and basophiles chemotactic activity. In addition IL-8 can induce histamine release from basophils from both normal and atopic individuals GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, Groα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al, *FEBS Lett.* 307, 97 (1992); Miller et al, *Crit. Rev. Immunol.* 12, 17 (1992); Oppenheim et al, *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis. Strieter et al, *Science* 258, 1798 (1992).

In vitro, IL-8, Groα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the B-receptor. Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GRO-α, GROβ, GROγ and NAP-2. See Holmes et al., supra; Murphy et al., *Science* 253, 1280 (1991); Lee et al., *J. Biol. Chem.* 267, 16283 (1992); LaRosa et al., *J. Biol. Chem.* 267, 25402 (1992); and Gayle et al., *J. Biol. Chem.* 268, 7283 (1993).

There remains a need for treatment, in this field, for compounds which are capable of binding to the IL-8 α or β receptor. Therefore, conditions associated with an increase in IL-8 production (which is responsible for chemotaxis of neutrophil and T-cells subsets into the inflammatory site) would benefit by compounds which are inhibitors of IL-8 receptor binding.

SUMMARY OF THE INVENTION

This invention provides for a method of treating a chemokine mediated disease, wherein the chemokine is one which binds to an IL-8 α or β receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

Compounds of Formula (I) useful in the present invention are represented by the structure:

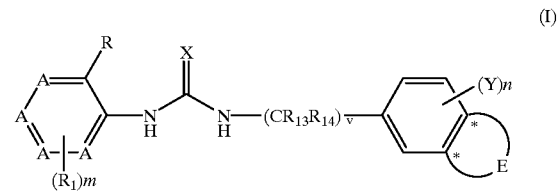

(I)

wherein

X is oxygen or sulfur;

A is nitrogen, provided that only one or two of the A moieties are nitrogen and the remainder are carbon substituted by hydrogen or $R_1$;

R is any functional moiety having an ionizable hydrogen and a pKa of 10 or less;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)q$ $S(O)_tR_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heterocyclic, heterocyclic $C_{1-4}$alkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$ alkenyl $C(O)$ $NR_4R_5$; $(CR_8R_8)q$ $C(O)NR_4R_5$; $(CR_8R_8)q$ $C(O)$ $NR_4R_{10}$; $S(O)_3H$; $S(O)_3R_8$; $(CR_8R_8)q$ $C(O)R_{11}$; $C_{2-10}$ alkenyl $C(O)R_{11}$; $C_{2-10}$ alkenyl $C(O)OR_{11}(CR_8R_8)q$ $C(O)OR_{12}$; $(CR_8R_8)q$ $OC(O)R_{11}$; $(CR_8R_8)qNR_4C(O)$ $R_{11}$, $(CR_8R_8)q$ $NHS(O)_2R_{17}$, $(CR_8R_8)q$ $S(O)_2NR_4R_5$; or two $R_1$ moieties together may form $O—(CH_2)_sO—$ or a 5 to 6 membered unsaturated ring;

q is 0, or an integer having a value of 1 to 10;

t is 0, or an integer having a value of 1 or 2;

s is an integer having a value of 1 to 3;

v is 0, or an integer having a value of 1 to 4;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic $C_{1-4}$ alkyl, or $R_4$ and $R_5$ together with the nitrogen to which they are attached form a 5 to 7 member ring which may optionally comprise an additional heteroatom selected from O/N/S;

Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)q$ $S(O)_tR_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heteroaryl $C_{1-4}$ alkyloxy; heterocyclic, heterocyclic $C_{1-4}$alkyl; aryl $C_{2-10}$ alkenyl; heteroaryl $C_{2-10}$ alkenyl; heterocyclic $C_{2-10}$ alkenyl; $(CR_8R_8)q$ $NR_4R_5$; $C_{2-10}$ alkenyl $C(O)$ $NR_4R_5$; $(CR_8R_8)q$ $C(O)NR_4R_5$; $(CR_8R_8)q$ $C(O)$ $NR_4R_{10}$; $S(O)_3H$; $S(O)_3R_8$; $(CR_8R_8)q$ $C(O)R_{11}$; $C_{2-10}$ alkenyl $C(O)R_{11}$; $C_{2-10}$ alkenyl $C(O)OR_{11}$; $C(O)R_{11}$; $(CR_8R_8)q$ $C(O)OR_{12}$; $(CR_8R_8)q$ $OC(O)R_{11}$; $(CR_8R_8)q$ $NR_4C(O)R_{11}$, $(CR_8R_8)q$ $NHS(O)_2R_d$, $(CR_8R_8)q$ $S(O)_2NR_4R_5$; or two Y moieties together may form $O—(CH_2)_sO—$ or a 5 to 6 membered unsaturated ring;

$R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur;

n is an integer having a value of 1 to 3;

m is an integer having a value of 1 to 3;

$R_8$ is hydrogen or $C_{1-4}$ alkyl;

$R_{10}$ is $C_{1-10}$ alkyl $C(O)_2R_8$;

$R_{11}$ is hydrogen, $C_{1-4}$ alkyl, optionally substituted aryl, optionally substituted aryl $C_{1-4}$alkyl, optionally substituted heteroaryl, optionally substituted heteroaryl $C_{1-4}$alkyl, optionally substituted heterocyclic, or optionally substituted heterocyclic $C_{1-4}$alkyl;

$R_{12}$ is hydrogen, $C_{1-10}$ alkyl, optionally substituted aryl or optionally substituted arylalkyl;

$R_{13}$ and $R_{14}$ are independently hydrogen, optionally substituted $C_{1-4}$ alkyl, or one of $R_{13}$ and $R_{14}$ may be optionally substituted aryl;

$R_{17}$ is $C_{1-4}$alkyl, aryl, arylalkyl, heteroaryl, heteroaryl $C_{1-4}$alkyl, heterocyclic, or heterocyclic $C_{1-4}$alkyl, wherein the aryl, heteroaryl and heterocyclic rings may all be optionally substituted;

$R_d$ is $NR_6R_7$, alkyl, aryl $C_{1-4}$alklyl, aryl $C_{2-4}$ alkenyl, heteroaryl, hetroaryl-$C_{1-4}$alkyl, heteroaryl $C_{2-4}$ alkenyl, heterocyclic, heterocyclic $C_{1-4}$ alkyl, wherein the aryl, heteroaryl and heterocyclic rings may all be optionally substituted;

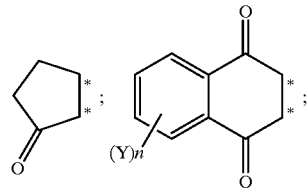

E is optionally selected from

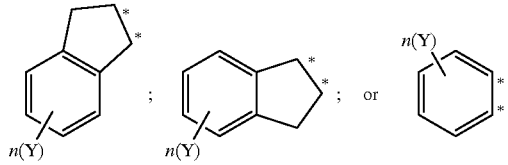

denoting point of attachment of the ring;

or a pharmaceutically acceptably salt thereof.

DETAILED DESCRIPTION OF THE INVENTION

The compounds of Formula (I) may also be used in association with the veterinary treatment of mammals, other than humans, in need of inhibition of IL-8 or other chemokines which bind to the IL-8 α and β receptors. Chemokine mediated diseases for treatment, therapeutically or prophylactically, in animals include disease states such as those noted herein in the Methods of Treatment section.

In compounds of Formula (I), R is suitably any functional moiety which provides an ionizable hydrogen having a pKa of 10 or less, preferably from about 3 to 9, more preferably from about 3 to 7. Such functional groups include, but are not limited to, hydroxy, carboxylic acid, thiol, $—SR_2—OR_2$, $—NH—C(O)R_a$, $—C(O)NR_6R_7$, a substituted sulfonamides of the formula $—NHS(O)_2R_b$, $—S(O)_2NHR_c$, $NHC(X_2)$ $NHR_b$, or a tetrazolyl; wherein $X_2$ is oxygen or sulfur, preferably oxygen. Preferably, the functional group is other than a sulfonic acid. either directly or as a substituent group on the aryl, heteroaryl, or heterocyclic moiety ring, such as in $SR_2$ or $OR_2$. More preferably R is OH, SH, or $NHS(O)_2$ $R_b$.

Suitably, $R_2$ is a substituted aryl, heteroaryl, or heterocyclic ring, which ring contains a functional moiety providing an ionizable hydrogen having a pKa of 10 or less.

Suitably, $R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur. This heteroring may be optionally substituted as defined herein.

Suitably Ra is an alkyl, aryl, aryl$C_{1-4}$alkyl, heteroaryl, heteroaryl$C_{1-4}$alkyl, heterocyclic, or a heterocyclic $C_{1-4}$alkyl moiety, all of which may be optionally substituted, as defined herein below.

Suitably, $R_b$ is a $NR_6R_7$, alkyl, aryl, aryl$C_{1-4}$alkyl, aryl$C_{2-4}$alkenyl, heteroaryl, heteroaryl$C_{1-4}$alkyl, heteroaryl$C_{2-4}$alkenyl, heterocyclic, or heterocyclic $C_{1-4}$alkyl, or a heterocyclic $C_{2-4}$alkenyl moiety, camphor, all of which may be optionally substituted one to three times independently by halogen; nitro; halosubstituted $C_{1-4}$ alkyl, such as $CF_3$; $C_{1-4}$ alkyl, such as methyl; $C_{1-4}$ alkoxy, such as methoxy; $NR_9C(O)R_a$; $C(O)NR_6R_7$, $S(O)_3H$, or $C(O)OC_{1-4}$ alkyl. $R_b$ is preferably an optionally substituted phenyl, benzyl, or styryl. When $R_b$ is a heteroaryl, it is preferably an optionally substituted thiazole, an optionally substituted thienyl, or an optionally substituted quinolinyl ring.

Suitably, $R_9$ is hydrogen or a $C_{1-4}$ alkyl. Preferably, $R_9$ is hydrogen. Suitably when the $R_b$ substituent group is $NR_9C(O)R_a$, then $R_a$ is preferably an alkyl group, such as methyl.

Suitably $R_c$ is hydrogen, alkyl, aryl, aryl$C_{1-4}$alkyl, aryl$C_{1-4}$alkenyl, heteroaryl, heteroaryl$C_{1-4}$alkyl, heteroaryl$C_{1-4}$alkenyl, heterocyclic, or heterocyclic $C_{1-4}$alkyl, or a heterocyclic $C_{1-4}$alkenyl moiety, all of which may be optionally substituted one to three times independently by halogen, nitro, halosubstituted $C_{1-4}$ alkyl, $C_{1-4}$ alkyl, $C_{1-4}$ alkoxy, $NR_9C(O)R_a$, $C(O)NR_6R_7$, $S(O)_3H$, or $C(O)OC_{1-4}$ alkyl. Preferably, $R_c$ is an optionally substituted phenyl.

When R is an $OR_2$ or $SR_2$ moiety it is recognized by one of skill in the art that the aryl ring must, therefore, contain the required ionizable hydrogen. The aryl ring may also be additionally substituted, independently, by one to three groups, which groups may also contain an additional ionizable group, and which include but are not limited to, halogen, nitro, halosubstituted $C_{1-4}$ alkyl, $C_{1-4}$ alkyl, $C_{1-4}$ alkoxy, hydroxy, SH, —$C(O)NR_6R_7$, —NH—$C(O)R_a$, —$NHS(O)_2R_b$, $S(O)_2NR_6R_7$, $C(O)OR_8$, or a tetrazolyl ring.

In compounds of Formula (I), suitably $R_1$ is independently selected from hydrogen; halogen; nitro; cyano; halosubstituted $C_{1-10}$ alkyl, such as $CF_3$; $C_{1-10}$ alkyl, such as methyl, ethyl, isopropyl, or n-propyl; $C_{2-10}$ alkenyl; $C_{1-10}$ alkoxy, such as methoxy, or ethoxy; halosubstituted $C_{1-10}$ alkoxy, such as trifluoromethoxy; azide; $(CR_8R_8)q\ S(O)_tR_4$, wherein t is 0, 1 or 2; hydroxy; hydroxy $C_{1-4}$alkyl, such as methanol or ethanol; aryl, such as phenyl or naphthyl; aryl $C_{1-4}$ alkyl, such as benzyl; aryloxy, such as phenoxy; aryl $C_{1-4}$ alkyloxy, such as benzyloxy; heteroaryl; heteroarylalkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$ alkenyl $C(O)NR_4R_5$; $(CR_8R_8)q\ C(O)NR_4R_5$; $(CR_8R_8)q\ C(O)NR_4R_{10}$; $S(O)_3H$; $S(O)_3R_8$; $(CR_8R_8)q\ C(O)R_{11}$; $C_{2-10}$ alkenyl $C(O)R_{11}$; $C_{2-10}$ alkenyl $C(O)OR_{11}$; $C(O)R_{11}$; $(CR_8R_8)q\ C(O)OR_{12}$; $(CR_8R_8)qOC(O)R_{11}$; $(CR_8R_8)q\ NR_4C(O)R_{11}$, $(CR_8R_8)q\ NHS(O)_2R_{17}$, $(CR_8R_8)qS(O)_2NR_4R_5$; or $R_1$ moieties together may form O—$(CH_2)_s$O— or a 5 to 6 membered unsaturated ring; and s is an integer having a value of 1 to 3. The aryl, arylalkyl, arylalkenyl, heteroaryl, heteroarylalkyl, heteroarylalkenyl, heterocyclic, heterocyclicalkyl, and heterocyclicalkenyl moieties may all be optionally substituted as defined herein below.

Suitably, q is 0, or an integer having a value of 1 to 10.

When $R_1$ forms a dioxybridge, s is preferably 1. When $R_1$ forms an additional unsaturated ring, it is preferably 6 membered resulting in a naphthylene ring system. This naphthylene ring may be substituted independently, 1 to 3 times by the other $R_1$ moieties as defined above.

Suitably, $R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S.

$R_8$ is suitably independently selected from hydrogen or $C_{1-4}$ alkyl.

$R_{10}$ is suitably $C_{1-10}$ alkyl $C(O)_2R_8$, such as $CH_2C(O)_2H$ or $CH_2C(O)_2CH_3$.

$R_{11}$ is suitably hydrogen, $C_{1-4}$ alkyl, aryl, aryl $C_{1-4}$ alkyl, heteroaryl, heteroaryl $C_{1-4}$alkyl, heterocyclic, or heterocyclic $C_{1-4}$alkyl.

$R_{12}$ is suitably hydrogen, $C_{1-10}$ alkyl, optionally substituted aryl or optionally substituted arylalkyl.

$R_{17}$ is suitably $C_{1-4}$alkyl, aryl, arylalkyl, heteroaryl, heteroaryl$C_{1-4}$alkyl, heterocyclic, or heterocyclic$C_{1-4}$alkyl, wherein the aryl, heteroaryl and heterocyclic rings may all be optionally substituted.

Preferably $R_1$ is halogen, cyano, nitro, $CF_3$, $C(O)NR_4R_5$, alkenyl $C(O)NR_4R_5$, $C(O)R_4R_{10}$, alkenyl $C(O)OR_{12}$, heteroaryl, heteroarylalkyl, heteroaryl alkenyl, or $S(O)NR_4R_5$, and preferably $R_4$ and $R_5$ are both hydrogen or one is phenyl. A preferred ring substitution for $R_1$ is in the 4-position of the phenyl ring.

When R is OH, SH or $NSO_2R_b$ than $R_1$ is preferably substituted in the 3-position, the 4-position or di substituted in the 3,4-position. The substituent group is suitably an electron withdrawing moiety. Preferably when R is OH, SH or $NSO_2R_b$, than $R_1$ is nitro, halogen, cyano, trifluoromethyl group, $C(O)NR_4R_5$.

When R is carboxylic acid, than $R_1$ is preferably hydrogen, or $R_1$ is preferably substituted in the 4-position, more preferably substituted by trifluoromethyl or chloro.

In compounds of Formula (I), suitably $R_{13}$ and $R_{14}$ are independently hydrogen, optionally substituted $C_{1-4}$ alkyl which may be straight or branched as defined herein, or one of $R_{13}$ and $R_{14}$ are an optionally substituted aryl; v is an integer having a value of 1 to 4.

When $R_{13}$ or $R_{14}$ are an optionally substituted alkyl, the alkyl moiety may be substituted one to three times independently by halogen; halosubstituted $C_{1-4}$ alkyl such as triflouromethyl; hydroxy; hydroxy $C_{1-4}$alkyl, $C_{1-4}$ alkoxy; such as methoxy, or ethoxy, halosubstituted $C_{1-10}$ alkoxy, $S(O)_tR_4$; aryl; $NR_4R_5$; $NHC(O)R_4$; $C(O)NR_4R_5$; or $C(O)OR_8$.

Suitably, Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)q\ S(O)_tR_4$; hydroxy; hydroxy$C_{1-4}$ alkyl; aryl; aryl $C_{1-4}$ alkyl; aryloxy; aryl$C_{1-4}$ alkyloxy; heteroaryl; heteroarylalkyl; heteroaryl $C_{1-4}$ alkyloxy; heterocyclic, heterocyclic $C_{1-4}$alkyl; aryl $C_{2-10}$ alkenyl; heteroaryl $C_{2-10}$ alkenyl; heterocyclic $C_{2-10}$ alkenyl; $(CR_8R_8)q\ NR_4R_5$; $C_{2-10}$ alkenyl $C(O)NR_4R_5$; $(CR_8R_8)q\ C(O)NR_4R_5$; $(CR_8R_8)q\ C(O)NR_4R_{10}$; $S(O)_3H$; $S(O)_3R_8$; $(CR_8R_8)q\ C(O)R_{11}$; $C_{2-10}$ alkenyl $C(O)R_{11}$; $C_{2-10}$ alkenyl $C(O)OR_{11}$; $(CR_8R_8)q\ C(O)OR_{12}$; $(CR_8R_8)q\ OC(O)R_{11}$; $(CR_8R_8)q\ NR_4C(O)R_{11}$, $(CR_8R_8)q\ NHS(O)_2R_d$, $(CR_8R_8)q\ S(O)_2NR_4R_5$ or two Y moieties together may form O—$(CH_2)_s$O— or a 5 to 6 membered unsaturated ring When Y forms a dioxybridge, s is preferably 1. When Y forms an additional unsaturated ring, it is preferably 6 membered resulting in a naphthylene ring system. This naphthylene ring may be substituted 1 to 3 times by other Y moieties as defined above. The aryl, arylalkyl, arylalkenyl, heteroaryl, heteroarylalkyl, heteroarylalkenyl, heterocyclic, heterocyclicalkyl, and heterocyclicalkenyl moieties noted above may all be optionally substituted as defined herein.

Suitably, $R_d$ is a $NR_6R_7$, alkyl, aryl $C_{1-4}$ alkyl, aryl$C_{2-4}$ alkenyl, heteroaryl, hetroaryl-$C_{1-4}$alkyl, heteroaryl$C_{2-4}$ alkenyl, heterocyclic, heterocyclic$C_{1-4}$ alkyl, or heterocyclic $C_{2-4}$ alkenyl moiety, wherein the aryl, arylalkyl, arylalkenyl, heteroaryl, heteroarylalkyl, heteroarylalkenyl, heterocyclic, and heterocyclicalkyl, and heterocyclicalkenyl moieties noted above may all be optionally substituted as defined herein.

Y is preferably a halogen, $C_{1-4}$ alkoxy, optionally substituted aryl, optionally substituted aryloxy or arylalkoxy, methylene dioxy, $NR_4R_5$, thio $C_{1-4}$alkyl, thioaryl, halosubstituted alkoxy, optionally substituted $C_{1-4}$ alkyl, or hydroxy alkyl. Y is more preferably mono-substituted halogen, disubstituted halogen, mono-substituted alkoxy, disubstituted alkoxy, methylenedioxy, aryl, or alkyl, more preferably these groups are mono or di-substituted in the 2'-position or 2'-, 3'-position.

While Y may be substituted in any of the 5 ring positions, preferably when R is OH, SH, or $NSO_2R_b$, Y is preferably mono-substituted in the 2'-position or 3'-position, with the 4'-preferably being unsubstituted. If the ring is disubstituted, when R is OH, SH, or $NSO_2R_b$, substituents are preferably in the 2' or 3' position of a monocyclic ring. While both $R_1$ and Y can both be hydrogen, it is prefered that at least one of the rings be substituted, preferably both rings are substituted.

In compounds of Formula (I), X is suitably oxygen or sulfur, preferably oxygen.

The E ring denoted by its point of attachment through the asterix (*) may optionally be present. If the E ring is not present, than the ring is a phenyl moiety which is substituted by the Y terms as shown. The E ring may be substituted by the Y moiety in any ring, saturated or unsaturated, and is shown for purposes herein substituted only in the unsaturated ring(s).

The A containing ring, depicted below represents a substituted pyridyl or pyrimidine ring.

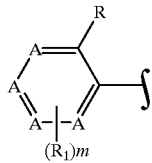

For instance, as only one or two A moieites may be nitrogen, this would yield a 3, 4, 5, or 6-pyridyl ring, or a 2,4- or 3,5-pyrimidine ring. The ring may be substituted by $R_1$ as noted above, yielding such rings as 2,4-dihydroxy-3,5-pyrimidyl; 2-hydroxy-4-sufanilamide-3,5-pyrimidyl; 2-hydroxy-4-sulfhydryl-6-amino- 3,5-pyrimidyl; 3-hydroxypyridin-2-yl; 2-hydroxyl-3-pyridyl; 2,4,-dihydroxy-6-methyl-5-pyridyl; 2-hydroxy-5-pyridyl or 2-sulfhydryl-5-pyridyl.

Exemplified compounds of Formula (I) include:

N-[2-hydroxy-4-sulfanilamide-3,5-pyrimidyl]-N'-[2-bromophenyl]urea

N-[2-sulfhydryl-5-pyridyl]-N'-[2-bromophenyl]urea

N-[2-hydroxy-3-pyridyl]-N'-[2-bromophenyl]urea

Additionally exemplied compound include:

N-[2-Hydroxy-5-pyridyl]-N'-[2-bromophenyl]urea

N-[2-Sulfhydryl-3-pyridyl]-N'-[2-bromophenyl]urea

N-(2,4-Dihydroxy-3,5-pyrimidyl)-N'-(2-bromophenyl)urea

N-(2-Hydroxy-4-sulfydryl-6-amino-3,5-pyrimidyl)-N'-(2-bromophenyl)urea

As used herein, "optionally substituted" unless specifically defined shall mean such groups as halogen, such as fluorine, chlorine, bromine or iodine; hydroxy; hydroxy substituted $C_{1-10}$alkyl; $C_{1-10}$ alkoxy, such as methoxy or ethoxy; $S(O)_{m'}C_{1-10}$ alkyl, wherein m' is 0, 1 or 2, such as methyl thio, methyl sulfinyl or methyl sulfonyl; amino, mono & di-substituted amino, such as in the $NR_4R_5$ group; $NHC(O)R_4$; $C(O)NR_4R_5$; $C(O)OH$; $S(O)_2NR_4R_5$; $NHS(O)_2R_{15}$, $C_{1-10}$ alkyl, such as methyl, ethyl, propyl, isopropyl, or t-butyl; halosubstituted $C_{1-10}$ alkyl, such $CF_3$; an optionally substituted aryl, such as phenyl, or an optionally substituted arylalkyl, such as benzyl or phenethyl, optionally substituted heterocylic, optionally substituted heterocylicalkyl, optionally substituted heteroaryl, optionally substituted heteroaryl alkyl, wherein these aryl , hetroaryl, or heterocyclic moieties may be substituted one to two times by halogen; hydroxy; hydroxy substituted alkyl; $C_{1-10}$ alkoxy; $S(O)_{m'}C_{1-10}$ alkyl; amino, mono & di-substituted amino, such as in the $NR_4R_5$ group; $C_{1-10}$ alkyl, or halosubstituted $C_{1-10}$ alkyl, such as $CF_3$.

$R_{15}$ is suitably $C_{1-4}$ alkyl, aryl, aryl $C_{1-4}$alkyl, heteroaryl, heteroaryl$C_{1-4}$alkyl, heterocyclic, or heterocyclic$C_{1-4}$alkyl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo" —-all halogens, that is chloro, fluoro, bromo and iodo.

"$C_{1-10}$alkyl" or "alkyl" —- both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl" —-phenyl and naphthyl;

"heteroaryl" (on its own or in any combination, such as "heteroaryloxy", or "heteroaryl alkyl")— a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclicalkyl")— a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl" —the oxide S (O) of the corresponding sulfide, the term "thio" refers to the sulfide, and the term "sulfonyl" refers to the fully oxidized $S(O)_2$ moiety.

The term "wherein two $R_1$ moieties (or two Y moieties) may together form a 5 or 6 membered unsaturated ring" is used herein to mean the formation of a napthylene ring system or a phenyl moiety having attached a 6 membered partially unsaturated ring such as a $C_6$ cycloalkenyl, i.e hexene, or a $C_5$ cyloalkenyl moiety, cyclopentene.

The compounds of Formula (I) may be obtained by applying synthetic procedures, some of which are illustrated in the Schemes below. The synthesis provided for in these Schemes is applicable for the producing compounds of Formula (I) having a variety of different R, $R_1$, and Aryl groups which are reacted, employing optional substituents which are suitably protected, to achieve compatibility with the reactions outlined herein. Subsequent deprotection, in those cases, then affords compounds of the nature generally disclosed. Once the urea nucleus has been established, further compounds of these formulas may be prepared by applying standard techniques for functional group interconversion, well known in the art. While the schemes are shown with compounds only of Formula (I) this is merely for illustration purposes only.

Methods of Preparation

The hydroxy aniline, and the thio aniline can be purchased commercially, be obtained as outlined in EP 82 302824 whose disclosure is incorporated herein by reference, or it may be obtained as outlined below in scheme 1. The commercially available pyridone can be nitrated with nitric acid or other strong nitrating agents like nitrosonium tetrafluoroborate. The resulting nitro phenol can be chlorinated to form 2, scheme 1 with phosphorous pentachloride or other chlorinating agents like thionyl chloride. The chloride can then be converted to the corresponding thiophenol with hydrogen sulfide in the presence of a base such as NaOH or triethyl amine. Finally the nitro group can be reduced by standard procedures like $SnCl_2$, Pd/C and hydrogen gas or Zn to form the thio aniline 3.

Scheme 1

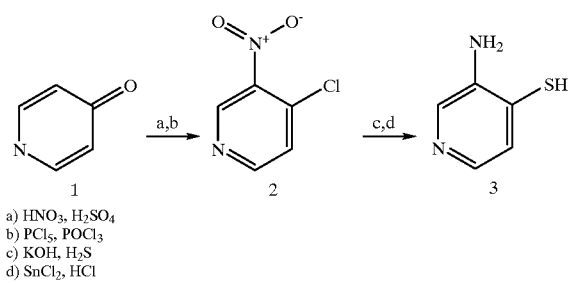

a) $HNO_3$, $H_2SO_4$
b) $PCl_5$, $POCl_3$
c) KOH, $H_2S$
d) $SnCl_2$, HCl

This thio aniline or hydroxy aniline can then be converted to the urea 4 by condensation with a commercially available isocyanate (scheme 2).

Scheme 2

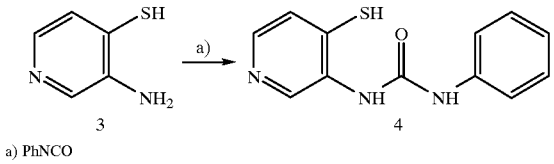

a) PhNCO

Alternatively, as shown below in Scheme 3 the 2-hydroxy 1-amino heterocycle can be protected by reagents known in the art such as tert(butyl)dimethylsilyl chloride and imidazole in an aprotic solvent like DMF (scheme 3). The aniline can then be reacted with a phosgene equivalent like triphosgene or carbonyl diimidazole in the presence of a base such as sodium bicarbonate to form the isocyanate 6 (or with thiophosgene to form the thioisocyanate). This isocyanate can then be condensed with the desired amine which can be purchased commercially. The protected phenol can then be deprotected by standard conditions such as triethyl amine hydrofluoride to form the urea 7.

Scheme 3

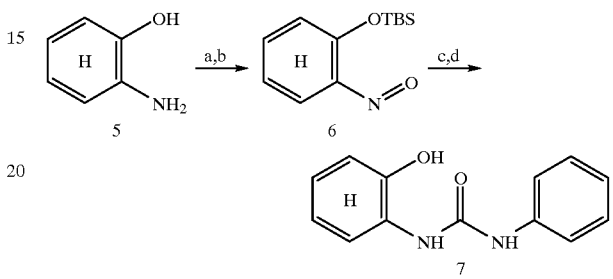

Scheme 4

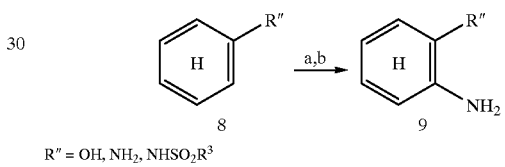

$R'' = OH, NH_2, NHSO_2R^3$
a) $HNO_3$
b) $SnCl_2$

If the desired 2-substituted heterocyclic amine 11-scheme 4, is not commercially available the corresponding nitro compound can be prepared from 10-scheme 4, under standard nitration conditions (using $HNO_3$ or $BF_4NO_3$) at 23° C. The isomeric nitro compounds can then be separated by chromatography. The nitro compound is then reduced to the corresponding aniline 11-scheme 4 using $SnCl_2$ in EtOH(or alternately $H_2$/Pd or $LiAlH_4$).

Scheme 5

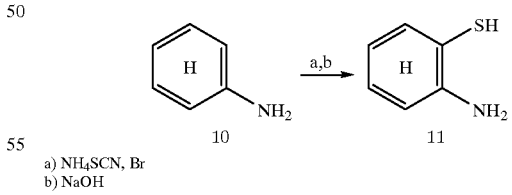

a) $NH_4SCN$, Br
b) NaOH

The desired 2-amino heterocyclic thiol 11-scheme 5 can also be synthesized by treatment of the heterocyclic amine with the thiocyanate anion in the presence of an oxidant(like bromine) to produce the 2-amino benzthiazole. After separation of the isomeric thiazoles by chromatography the desired thiazole can then be hydrolyzed to the desired 2-amino 1-thiol heterocycle 11-scheme 5 with a strong base like NaOH in a protic solvent (i.e., EtOH).

Scheme 6

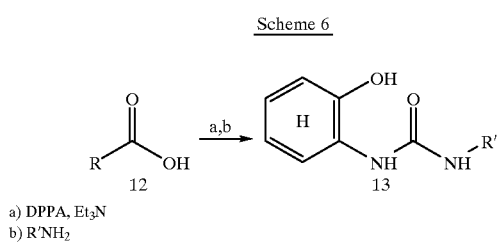

a) DPPA, Et₃N
b) R'NH₂

Alternatively the isocyanate can be synthesized from the corresponding carboxylic acid using the Curtius rearrangement (dppa and triethyl amine, oxalyl chloride followed by sodium azide, scheme 6). This isocyanate can then be condensed with the 1-amino 2-hydroxy heterocycle to form urea 13 (scheme 6).

Pharmaceutically acceptable salts of compounds of Formula (I) may be obtained in known manner, for example by treatment thereof with an appropriate amount of acid or base in the presence of a suitable solvent.

Numerous conversions of aryl halides to aryl cyano derivatives with copper (I) cyanide have been published. However, no examples of an aryl ring with a hydroxy group present were mentioned. Several attempts to obtain a cyano phenol moiety with published results failed. Using known conditions of elevated temperatures, greater than 170° C., such as from 180 to 210° did not yield displacement of the halogen to a cyano moiety. Standard bases, such as DMF and pyridine further provided no desired product. Intermediates such as 2-amino-5-fluorophenol, 2-nitro-5-fluorophenol, 2-nitro-5-methyl-6-bromophenol were tried with a change of halogens, from fluorine to chlorine to bromine, and with use of copper (I) cyanide. The use of a bromine derivative, such as 2-nitro-5-methyl-6-bromophenol, with dimethylfonnamide and using triethylamine with a catalytic amount of dimethylamino pyridine and copper (I) cyanide at reduced temperatures,. i.e. <100° C., preferably 60 to about 80° C. for reduced times from strandarized procedures, i.e., <18 hours, preferably about 4 to 6 hours yielded the desired products.

In the Examples, all temperatures are in degrees Centigrade (°C.). Mass spectra were performed upon a VG Zab mass spectrometer using fast atom bombardment, unless otherwise indicated. $^1$H-NMR (hereinafter "NMR") spectra were recorded at 250 MHz or 400MHz using a Bruker AM 250 or Am 400 spectrometer, respectively. Multiplicities indicated are: s=singlet, d=doublet, t=triplet, q=quartet, m=multiplet and br indicates a broad signal. Sat. indicates a saturated solution, equiv. indicates the proportion of a molar equivalent of reagent relative to the principal reactant.

Flash chromatography is run over Merck Silica gel 60 (230–400 mesh).

SYNTHETIC EXAMPLES

The invention will now be described by reference to the following examples which are merely illustrative and are not to be construed as a limitation of the scope of the present invention. All temperatures are given in degrees centigrade, all solvents used herein are of the highest available purity and all reactions are run under anhydrous conditions in an argon atmosphere unless otherwise indicated.

General Method A: Synthesis of N, N'-diphenyl urea To a solution of phenyl isocyanate(1.0 equiv.) in dimethyl formamide (1 ml) the corresponding aniline (1.0 equiv.) was added. The reaction mixture was stirred at 80° C. until complete (24–48 hrs.), then the solvent was removed under vacuum. The purification, yields and spectral characteristics for each individual compound are listed below.

Example 1

Preparation of N-[2-hydroxy-3-pyridyl]-N'-[2-bromophenyl]urea a)Preparation of 2-amino-3-hydroxypyridine To a solution of 2-hydroxy-3-nitropyridine (5 g, 45.4 mmol) in methanol(250 ml) was added 10% Pd/C (1 g). The mixture was flushed with argon, then hydrogen was bubbled through the solution for 10 min. and a hydrogen atmosphere was maintained at balloon pressure overnight. The mixture was filtered through celite and the celite was washed with methanol. The solvent was evaporated and chromatography of the resulting solid on silica gel (5% MeOH/CH₂Cl₂) gave the desired product(3.2 g, 89%). $^1$H NMR (CD₃OD): δ 6.96 (d, 1H), 6.90 (dd, 1H), 6.77 (d, 1H).

b)Preparation of N-[2-hydroxy-3-pyridyl]-N'-[2-bromophenyl]urea

N-[2-hydroxy-3-pyridyl]-N'-[2-bromophenyl] urea was prepared from 2-amino-3-hydroxypyridine(220 mg, 2.00 mmol) according to the procedure in General Method A. The product was purified by precipitation from methylene chloride/hexane(1 equiv./20 equiv.) and filtering. (510 mg, 83%). $^1$H NMR (CD₃OD): δ 8.24 (d, 1H), 7.85 (d, 1H), 7.55 (d, 1H), 7.31 (t, 1H), 7.02 (m, 2H), 6.34 (t, 1H).

Example 2

Preparation of N-[2-sulfhydryl-5-pyridyl]-N'-[2-bromophenyl]urea a) Preparation of 4-hydroxy-3-nitropyridine 4-Hydroxy-3-nitropyridine was prepared by addition of 4-pyridone (50 g, 0.532M) to a mixture of fuming nitric acid and sulfuric acid. The resulting solution was heated for 1 hour at 100° C. The solution was cooled and poured into 500 mL of ice water and the desired product was obtained as a solid. (mp. 280° C.)

b) Preparation of 4-chloro-3-nitropyridine

4-Chloro-3-nitropyridine was prepared from 4-hydroxy-3-nitropyridine(25 g, 0.179M), phosphorus pentachloride (40 g, 0.192M) and 1 mL of phosphorous oxytrichloride. The mixture was heated at 120° for 1 hour. The reaction mixture was diluted with chlorform/ethanol mixture(9/1) and the precipitate was filtered to afford desired. (mp. 153–154° C.)

c) Preparation of 3-nitro-4-sulfhydrylpyridine 4-chloro-3-nitropyridine (18 g, 0.114M) was added to a cooled solution of 10 g of potassium hydroxide and 70 mL of methanol saturated with hydrogen sulfide. The reaction stirred for 2 hours at 25° C. and the solvents were removed by vacuum. The residue was acidified and filtered. (mp. 132° C.)

d) Preparation of 3-amino-4-sulfhydrylpyridine

3-Nitro-4-sulfhydrylpyridine (6 g, 0.038M) was added to tin(II) chloride (50 g) in 50 mL of concentrated hydrogen chloride. The solution was stirred at 60 ° C. for 3 hours. The reaction mixture was diluted with water, neutralized with ammonium hydroxide and extracted. The organic layer was evaporated to yield the product. (mp. 200–203° C.)

b) Preparation of N-[2-sulfhydryl-5-pyridyl]-N'-[2-bromophenyl]urea

N-[2-sulfhydryl-5-pyridyl]-N'-[2-bromophenyl] urea was prepared from 3-amino-4-sulfhydrylpyridine (50 mg, 0.397 mmol) according to the procedure in General Method A. The product was purified by precipitation from methylene chloride/hexane(1 equiv./20 equiv.) and filtering. (65 mg, 51%). $^1$H NMR (CD$_3$OD): δ 7.93 (d, 1H), 7.60 (d, 1H), 7.32 (d, 1H), 7.07 (t, 1H), 7.02 (dd, 1H), 6.72 (d, 1H), 6.53 (t, 1H).

Example 3

Preparation of N-[2-hydroxy-4-sulfanilamide-3 5-pyrimidyl]-N'-[2-bromophenyl]urea N-[2-Hydroxy-4-sulfanilamide-3,5-pyrimidyl]-N'-[2-bromophenyl] urea was prepared from 4-hydroxy-5-amino-2-sulfanilamide-1,3 pyrimidine (50 mg, 0.178 mmol, pat EP 82-302824) according to the procedure in General Method A. The product was purified by precipitation from methylene chloride/hexane(1 equiv./20equiv.) and filtering. (54 mg, 64%). $^1$H NMR (CD$_3$OD): δ 8.43 (d, 1H), 7.96 (d, 1H), 7.85 (m, 4H), 7.62 (d, 1H), 7.45 (t, 1H), 7.04 (t, 1H).

By analagous methods to those indicated above, the following compounds may also be prepared:

Example 4—N-[2-Hydroxy-5-pyridyl]-N'-[2-bromophenyl]urea

Example 5—N-[2-Sulfhydryl-3-pyridyl]-N'-[2-bromophenyl]urea

Example 6—N-(2,4-Dihydroxy-3,5-pyrimidyl)-N'-(2-bromophenyl)urea

Example 7—N-(2-Hydroxy-4-sulfydryl-6-amino-3,5-pyrimidyl)-N'-(2-bromophenyl)urea Method of Treatment The compounds of Formula (I), or a pharmaceutically acceptable salt thereof can be used in the manufacture of a medicament for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 α or β receptor, also referred to as the type I or type II receptor.

Accordingly, the present invention provides a method of treating a chemokine mediated disease, wherein the chemokine is one which binds to an IL-8 α or β receptor and which method comprises administering an effective amount of a compound of Formula (I) or a pharmaceutically acceptable salt thereof. In particular, the chemokines are IL-8, GROα, GROβ, GROγ, NAP-2 or ENA-78.

The compounds of Formula (I) are administered in an amount sufficient to inhibit cytokine function, in particular IL-8, GROα, GROβ, GROγ, NAP-2 or ENA78, such that they are biologically regulated down to normal levels of physiological function, or in some case to subnormal levels, so as to ameliorate the disease state. Abnormal levels of IL-8, GROα, GROβ, GROγ, NAP-2 or ENA-78 for instance in the context of the present invention, constitute: (i) levels of free IL-8 greater than or equal to 1 picogram per mL; (ii) any cell associated IL-8, GROα, GROβ, GROγ, NAP-2 or ENA-78 above normal physiological levels; or (iii) the presence of IL-8, GROα, GROβ, GROγ, NAP-2 or ENA-78 above basal levels in cells or tissues in which IL-8, GROα, GROβ, GROγ, NAP-2 or ENA-78 respectively, is produced.

There are many disease states in which excessive or unregulated IL-8 production is implicated in exacerbating and/or causing the disease. Chemokine mediated diseases include psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis or undesired hematopoietic stem cells release.

These diseases are primarily characterized by massive neutrophil infiltration, T-cell infiltration, or neovascular growth, and are associated with increased IL-8, GROα, GROβ, GRCγ or NAP-2 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ or NAP-2 has the unique property of promoting neutrophil chemotaxis, enzyme release including but not limited to elastase release as well as superoxide production and activation. The α-chemokines but particularly, GROα, GROβ, GROγ or NAP-2, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., Nature 381, pp 661 (1996) and Koup et al., Nature 381, pp 667 (1996).

The present invention also provides for a means of treating, in an acute setting, as well as preventing, in those individuals deemed susceptible to, CNS injuries by the chemokine receptor antagonist compounds of formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this are has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., Stoke, Vol. 25., No. 7, pp 1481–88 (1994) whose disclosure is incorporated herein by reference.

Models of closed head injuries and treatment with mixed 5-LO/CO agents is discussed in Shohami et al., J. of Vaisc & Clinical Physiology and Pharmacology, Vol. 3, No. 2, pp. 99–107 (1992) whose disclosure is incorporated herein by reference. Treatment which reduced edema formation was found to improve functional outcome in those animals treated.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown to be inhibitors of type II IL-8 receptors.

As used herein, the term "IL-8 mediated disease or disease state" refers to any and all disease states in which IL-8, GROα, GROβ, GROγ, NAP-2 or ENA-78 plays a role, either by production of IL-8, GROα, GROβ, GROγ, NAP-2 or ENA-78 themselves, or by IL-8, GROα, GROβ, GROγ, NAP-2 or ENA-78 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "chemokine mediated disease or disease state" refers to any and all disease states in which a chemokine which binds to an IL-8 α or β receptor plays a role, such as but not limited to IL-8, GROα, GROβ, GROγ, NAP-2 or ENA-78. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to IL-8, GROα, GROβ, GROγ, NAP-2, ENA-78, IP-10, MIP-1α, MIP-β, PF4, and MCP 1,2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by nonsystemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The IL-8, and Gro-α chemokine inhibitiory effects of compounds of the present invention were determined by the following in vitro assay:

Receptor Binding Assays:

[$^{125}$I] IL-8 (human recombinant) was obtained from Amersham Corp., Arlington Heights, Ill., with specific activity 2000 Ci/mmol. Gro-α was obtained from NEN- New England Nuclear. All other chemicals were of analytical grade. High levels of recombinant human IL-8 type α and β receptors were individually expressed in Chinese hamster ovary cells as described previously (Holmes, et al., *Science*, 1991, 253, 1278). The Chinese hamster ovary membranes were homogenized according to a previously described protocol (Haour, et al., *J Biol Chem.*, 249 pp 2195–2205 (1974)). Except that the homogenization buffer was changed to 10 mM Tris-HCL, 1 mM MgSO4, 0.5mM EDTA (ethylene-diaminetetra-acetic acid), 1 mMPMSF (α-toluenesulphonyl fluoride), 0.5 mg/L Leupeptin, pH 7.5. Membrane protein concentration was determined using Pierce Co. micro-assay kit using bovine serum albumin as a standard. All assays were performed in a 96-well micro plate format. Each reaction mixture contained $^{125}$I IL-8 (0.25 nM) or $^{125}$I Gro-α and 0.5 μg/mL of IL-8Rα or 1.0 μg/mL of IL-8Rβ membranes in 20 mM Bis-Trispropane and 0.4 mM Tris HCl buffers, pH 8.0, containing 1.2 mM MgSO$_4$, 0.1 mM EDTA, 25 mM NaCl and 0.03% CHAPS. In addition, drug or compound of interest was added which had been pre-dissolved in DMSO so as to reach a final concentration of between 0.01 nM and 100 uM. The assay was initiated by addition of $^{125}$I-IL-8. After 1 hour at room temperature the plate was harvested using a Tomtec 96-well harvester onto a glass fiber filtermat blocked with 1% polyethylenirnine/ 0.5% BSA and washed 3 times with 25 mM NaCl, 10 mM TrisHCl, 1 mM MgSO$_4$, 0.5 mM EDTA, 0.03% CHAPS, pH 7.4. The filter was then dried and counted on the Betaplate liquid scintillation counter. The recombinant IL-8 Rα, or Type I, receptor is also referred to herein as the non-permissive receptor and the recombinant IL-8 Rβ, or Type II, receptor is referred to as the permissive receptor.

All of the exemplified compounds of Formulas (I) noted herein in the Synthetic Chemistry Section, demonstrated an IC$_{50}$ from about 45 to about <1 μg/mL in the permissive models for IL-8 receptor inhibition.

Chemotaxis Assay:

The in vitro inhibitory properties of these compounds are determined in the neutrophil chemotaxis assay as described in Current Protocols in Immunology, vol I, Suppl 1, Unit 6.12.3., whose disclosure is incorporated herein by reference in its entirety. Neutrophils where isolated from human blood as described in Current Protocols in Immunology Vol I, Suppl 1 Unit 7.23.1, whose disclosure is incorporated herein by reference in its entirety. The chemoattractants IL-8, GRO-α, GRO-β, GRO-γ and NAP-2 are placed in the bottom chamber of a 48 multiwell chamber (Neuro Probe, Cabin John, Md.) at a concentration between 0.1 and 100 nM. The two chambers are separated by a 5 um polycarbonate filter. When compounds of this invention are tested, they are mixed with the cells (0.001–1000 nM) just prior to the addition of the cells to the upper chamber. Incubation is allowed to proceed for between about 45 and 90 min at about 37° C. in a humidified incubator with 5% CO$_2$. At the end of the incubation period, the polycarbonate membrane is removed and the top side washed, the membrane then stained using the Diff Quick staining protocol (Baxter Products, McGaw Park, Ill., USA). Cells which have chemotaxed to the chemokine are visually counted using a microscope. Generally, four fields are counted for each sample, these numbers are averaged to give the average number of cells which had migrated. Each sample is tested in triplicate and each compound repeated at least four times.

To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay:

The compounds of this invention are tested for their ability to prevent Elastase release from human neutrophils. Neutrophils are isolated from human blood as described in Current Protocols in Immunology Vol 1, Suppl 1 Unit 7.23.1. PMNs $0.88 \times 10^6$ cells suspended in Ringer's Solution (NaCl 118, KCl 4.56, NaHCO3 25, KH2PO4 1.03, Glucose 11.1, HEPES 5 mM, pH 7.4) are placed in each well of a 96 well plate in a volume of 50 ul. To this plate is added the test compound (0.001–1000 nM) in a volume of 50 ul, Cytochalasin B in a volume of 50 ul (20 ug/ml) and Ringers buffer in a volume of 50 ul. These cells are allowed to warm (37° C., 5% CO2, 95% RH) for 5 min before IL-8, GROα, GROβ, GROγ or NAP-2 at a final concentration of 0.01–1000 nM was added. The reaction is allowed to proceed for 45 min before the 96 well plate is centrifuged (800×g 5 min) and 100 ul of the supernatant removed. This suppernatant is added to a second 96 well plate followed by an artificial elastase substrate (MeOSuc-Ala-Ala-Pro-Val-AMC, Nova Biochem, La Jolla, Calif.) to a final concentration of 6 ug/ml dissolved in phosphate buffered saline. Immediately, the plate is placed in a fluorescent 96 well plate reader (Cytofluor 2350, Millipore, Bedford, Mass.) and data collected at 3 min intervals according to the method of Nakajima et al *J. Biol Chem* 254 4027 (1979). The amount of Elastase released from the PMNs is calculated by measuring the rate of MeOSuc-Ala-Ala-Pro-Val-AMC degradation.

TNF-α in Traumatic Brain Injury Assay

The present assay provides for examination of the expression of tumor necrosis factor mRNA in specfic brain regions which follow experimentally induced lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1,6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA was isolated and Northern blot hybridization is performed and quantitated relative to an TNF-α positive control RNA (macrophage=100%). A marked increase of TNF-α MRNA expression is observed in LH (104±17% of positive control, p<0.05 compared with sham), LC (105±71%, p<0.05) and LA (69±8%, p<0.01) in the traumatized hemisphere 1 hr. following injury. An increased TNF-α, mRNA expression is also observed in LH (46±8%, p<0.05), LC (30±3%, p<0.01) and LA (32±3%, p<0.01) at 6 hr. which resolves by 24 hr. following injury. In the contralateral hemisphere, expression of TNF-α mRNA is increased in RH (46±2%, p<0.01), RC (4±3%) and RA (22±8%) at 1 hr. and in RH (28±11%), RC (7±5%) and RA (26±6%, p<0.05) at 6 hr. but not at 24 hr. following injury. In sham (surgery without injury) or naive animals, no consistent changes in expression of TNF-α mRNA are observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury model for IL-β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1,6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization was performed and the quantity of brain tissue IL-1β mRNA is presented as percent relative radioactivity of IL-1β positive macrophage RNA which was loaded on same gel. At 1 hr. following brain injury, a marked and significant increase in expression of IL-1β mRNA is observed in LC (20.0±0.7% of positive control, n=6, p<0.05 compared with sham animal), LH (24.5±0.9%, p<0.05) and LA (21.5±3.1%, p<0.05) in the injured hemisphere, which remained elevated up to 6 hr. post injury in the LC (4.0±0.4%, n=6, p<0.05) and LH (5.0±1.3%, p<0.05). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating a chemokine mediated disease state, wherein the chemokine binds to an IL-8 α or β receptor in a mammal, which comprises administering to said mammal an effective amount of a compound of the formula:

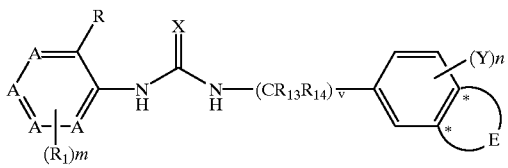

(I)

wherein

X is oxygen or sulfur;

A is nitrogen, provided that only one of the A moieties is a nitrogen and the remainder are carbon substituted by hydrogen or $R_1$;

R is hydroxy, carboxylic acid, thiol, —$SR_2$, —$OR_2$, —NH—C(O)$R_a$, —C(O)$NR_6R_7$, —NHS(O)$_2R_b$, —S(O)$_2$NHR$_c$, NHC(X$_2$)NHR$_b$, or tetrazolyl;

wherein $R_2$ is a substituted aryl, heteroaryl, or heterocyclic ring which ring contains a functional moiety providing an ionizable hydrogen having a pKa of 10 or less;

$R_a$ is an alkyl, aryl, aryl $C_{1-4}$alkyl, heteroaryl, heteroaryl $C_{1-4}$alkyl, heterocyclic, or a heterocyclic $C_{1-4}$alkyl moiety, all of which may be optionally substituted;

$R_b$ is $NR_6R_7$, alkyl, aryl, aryl$C_{1-4}$alkyl, aryl$C_{2-4}$ alkenyl, heteroaryl, heteroaryl$C_{1-4}$alkyl, heteroaryl$C_{2-4}$ alkenyl, heterocyclic, heterocyclic $C_{1-4}$alkyl, heterocyclic $C_{2-4}$alkenyl moiety, camphor, all of which may be optionally substituted one to three times independently by halogen; nitro; halosubstituted $C_{1-4}$ alkyl; $C_{1-4}$ alkyl; $C_{1-4}$ alkoxy; $NR_9$C(O)$R_a$; C(O)$NR_6R_7$, S(O)$_3$H, or C(O)O$C_{1-4}$ alkyl;

$R_9$ is hydrogen or a $C_{1-4}$ alkyl;

$R_c$ is alkyl, aryl, aryl$C_{1-4}$alkyl, aryl$C_{2-4}$alkenyl, heteroaryl, heteroaryl$C_{1-4}$alkyl, heteroaryl$C_{2-4}$ alkenyl, heterocyclic, heterocyclic $C_{1-4}$alkyl, or a heterocyclic $C_{2-4}$alkenyl moiety, all of which moieties may be optionally substituted one to three times independently by halogen, nitro, halosubstituted $C_{1-4}$ alkyl, $C_{1-4}$ alkyl, $C_{1-4}$ alkoxy, $NR_9$C(O)$R_a$, C(O)$NR_6R_7$, S(O)$_3$H, or C(O)O$C_{1-4}$ alkyl; and $X_2$ is oxygen or sulfur;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; (CR$_8$R$_8$)q S(O)$_t$R$_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heteroaryl $C_{1-4}$alkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; (CR$_8$R$_8$)qNR$_4$R$_5$; $C_{2-10}$ alkenyl C(O)NR$_4$R$_5$; (CR$_8$R$_8$)q C(O)NR$_4$R$_5$; (CR$_8$R$_8$)q C(O)NR$_4$R$_{10}$; S(O)$_3$H; S(O)$_3$R$_8$; (CR$_8$R$_8$)q C(O)R$_{11}$; $C_{2-10}$ alkenyl C(O)R$_{11}$; $C_{2-10}$ alkenyl C(O)OR$_{11}$(CR$_8$R$_8$)q C(O)OR$_{12}$; (CR$_8$R$_8$)q OC(O)R$_{11}$; (CR$_8$R$_8$)q NR$_4$C(O)R$_{11}$, (CR$_8$R$_8$)q NHS(O)$_2$R$_{17}$, (CR$_8$R$_8$)q S(O)$_2$NR$_4$R$_5$; or two $R_1$ moieties together may form O—(CH$_2$)$_s$O— or a 5 to 6 membered unsaturated ring;

q is 0, or an integer having a value of 1 to 10;

t is 0, or an integer having a value of 1 or 2;

s is an integer having a value of 1 to 3;

v is 0, or an integer having a value of 1 to 4;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic $C_{1-4}$ alkyl, or $R_4$ and $R_5$ together with the nitrogen to which they are attached form a 5 to 7 member ring which may optionally comprise an additional heteroatom selected from O/N/S;

Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; (CR$_8$R$_8$)q S(O)$_t$R$_4$; hydroxy; hydroxy$C_{1-4}$alkyl; aryl; aryl $C_{1-4}$ alkyl; aryloxy; aryl$C_{1-4}$ alkyloxy; heteroaryl; heteroarylalkyl; heteroaryl $C_{1-4}$alkyl; aryl $C_{2-10}$ alkenyl; heteroaryl $C_{2-10}$ alkenyl; heterocyclic $C_{2-10}$ alkenyl; (CR$_8$R$_8$)q NR$_4$R$_5$; $C_{2-10}$ alkenyl C(O)NR$_4$R$_5$; (CR$_8$R$_8$)q C(O)NR$_4$R$_5$; (CR$_8$R$_8$)q C(O)NR$_4$R$_{10}$; S(O)$_3$H; S(O)$_3$R$_8$; (CR$_8$R$_8$)q C(O)R$_{11}$; $C_{2-10}$ alkenyl C(O)R$_{11}$; $C_{2-10}$ alkenyl C(O)OR$_{11}$; C(O)R$_{11}$; (CR$_8$R$_8$)q C(O)OR$_{12}$; (CR$_8$R$_8$)q OC(O)R$_{11}$; (CR$_8$R$_8$)q NR$_4$C(O)R$_{11}$, (CR$_8$R$_8$)q NHS(O)$_2$R$_d$, (CR$_8$R$_8$)q S(O)$_2$NR$_4$R$_5$; or two Y moieties together may form O—(CH$_2$)$_s$O— or a 5 to 6 membered unsaturated ring;

$R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur;

n is an integer having a value of 1 to 3;

m is an integer having a value of 1 to 3;

$R_8$ is hydrogen or $C_{1-4}$ alkyl;

$R_{10}$ is $C_{1-10}$ alkyl C(O)$_2$R$_8$;

$R_{11}$ is hydrogen, $C_{1-4}$ alkyl, optionally substituted aryl, optionally substituted aryl $C_{1-4}$alkyl, optionally substituted heteroaryl, optionally substituted heteroaryl$C_{1-4}$ alkyl, optionally substituted heterocyclic, or optionally substituted heterocyclic$C_{1-4}$alkyl;

$R_{12}$ is hydrogen, $C_{1-10}$ alkyl, optionally substituted aryl or optionally substituted arylalkyl;

$R_{13}$ and $R_{14}$ are independently hydrogen, optionally substituted $C_{1-4}$ alkyl, or one of $R_{13}$ and $R_{14}$ may be optionally substituted aryl;

$R_{17}$ is $C_{1-4}$alkyl, aryl, arylalkyl, heteroaryl, heteroaryl$C_{1-4}$ alkyl, heterocyclic, or heterocyclic$C_{1-4}$alkyl, wherein the aryl, heteroaryl and heterocyclic rings may all be optionally substituted;

$R_d$ is $NR_6R_7$, alkyl, aryl$C_{1-4}$alklyl, aryl$C_{2-4}$ alkenyl, heteroaryl, hetroaryl-$C_{1-4}$alkyl, heteroaryl$C_{2-4}$ alkenyl, heterocyclic, heterocyclic$C_{1-4}$ alkyl, wherein the aryl, heteroaryl and heterocyclic rings may all be optionally substituted;

E is optionally selected from

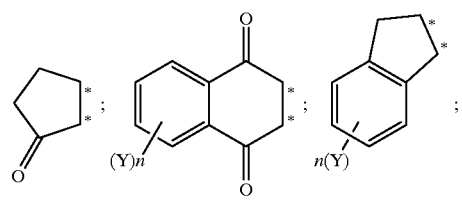

-continued

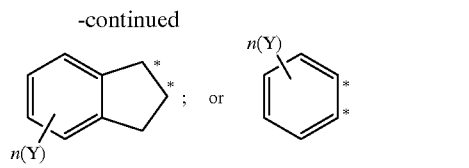

the asterix * denoting point of attachment of the ring, with at least one E being present;

or a pharmaceutically acceptably salt thereof.

2. The method according to claim 1 wherein the $R_2$ is optionally substituted one to three times by halogen, nitro, halosubstituted $C_{1-10}$ alkyl, $C_{1-10}$ alkyl, $C_{1-10}$ alkoxy, hydroxy, SH, —C(O)NR$_6$R$_7$, —NH—C(O)R$_a$, —NHS(O)$_2$R$_b$, S(O)NR$_6$R$_7$, C(O)OR$_8$, or a tetrazolyl ring.

3. The method according to claim 1 wherein R is OH, —NHS(O)$_2$R$_b$ or C(O)OH.

4. The method according to claim 1 wherein $R_1$ is halogen, cyano, nitro, CF$_3$, C(O)NR$_4$R$_5$, alkenyl C(O)NR$_4$R$_5$, C(O)R$_4$R$_{10}$, alkenyl C(O)OR$_{12}$, heteroaryl, heteroarylalkyl, heteroaryl alkenyl, or S(O)NR$_4$R$_5$.

5. The method according to claim 1 wherein Y is halogen, $C_{1-4}$ alkoxy, optionally substituted aryl, optionally substituted arylalkoxy, methylene dioxy, NR$_4$R$_5$, thioC$_{1-4}$alkyl, thioaryl, halosubstituted alkoxy, optionally substituted $C_{1-4}$alkyl, hydroxy alkyl.

6. The method according to claim 1 wherein the A containing ring is a pyridine ring.

7. The method according to claim 1 wherein R is OH, SH, or NHS(O)$_2$R$_b$ and $R_1$ is substituted in the 3-position, the 4-position or di-substituted in the 3,4-position by an electron withdrawing moiety.

8. The method according to claim 1 wherein the mammal is afflicted with a chemokine mediated disease selected from psoriasis, atopic dermatitis, asthma, chronic obstructive pulmonary disease, adult respiratory distress syndrome, arthritis, inflammatory bowel disease, Crohn's disease, ulcerative colitis, septic shock, endotoxic shock, gram negative sepsis, toxic shock syndrome, stroke, cardiac and renal reperfusion injury, glomerulo-nephritis, thrombosis, alzheimers disease, graft vs. host reaction, or allograft rejections.

9. A compound of the formula:

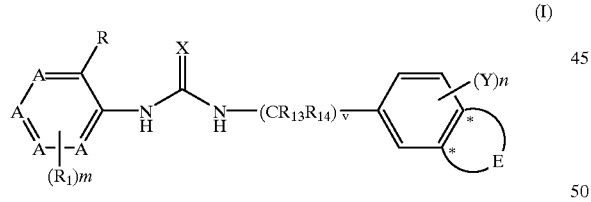

(I)

wherein

X is oxygen or sulfur;

A is nitrogen, provided that only one of the A moieties is a nitrogen and the remainder are carbon substituted by hydrogen or $R_1$;

R is hydroxy, carboxylic acid, thiol, —SR$_2$, —OR$_2$, —NH—C(O)R$_a$, —C(O)NR$_6$R$_7$, —NHS(O)$_2$R$_b$, —S(O)$_2$NHR$_c$, NHC(X$_2$)NHR$_b$, or tetrazolyl;

wherein $R_2$ is a substituted aryl, heteroaryl, or heterocyclic ring which ring contains a functional moiety providing an ionizable hydrogen having a pKa of 10 or less;

$R_a$ is an alkyl, aryl, aryl $C_{1-4}$alkyl, heteroaryl, heteroaryl $C_{1-4}$alkyl, heterocyclic, or a heterocyclic $C_{1-4}$alkyl moiety, all of which may be optionally substituted;

$R_b$ is NR$_6$R$_7$, alkyl, aryl arylC$_{1-4}$alkyl, arylC$_{2-4}$alkenyl, heteroaryl, heteroarylC$_{1-4}$alkyl, heteroarylC$_{2-4}$alkenyl, heterocyclic, heterocyclic C$_{1-4}$alkyl, heterocyclic C$_{2-4}$alkenyl moiety, camphor, all of which may be optionally substituted one to three times independently by halogen; nitro; halosubstituted $C_{1-4}$ alkyl; $C_{1-4}$ alkyl; $C_{1-4}$ alkoxy; NR$_9$C(O)R$_a$; C(O)NR$_6$R$_7$, S(O)$_3$H, or C(O)OC$_{1-4}$ alkyl;

$R_9$ is hydrogen or a $C_{1-4}$ alkyl;

$R_c$ is alkyl, aryl, arylC$_{1-4}$alkyl, arylC$_{2-4}$alkenyl, heteroaryl, heteroarylC$_{1-4}$alkyl, heteroarylC$_{2-4}$alkenyl, heterocyclic, heterocyclic C$_{1-4}$alkyl, or a heterocyclic C$_{2-4}$alkenyl moiety, all of which moieties may be optionally substituted one to three times independently by halogen, nitro, halosubstituted C$_{1-4}$ alkyl, C$_{1-4}$ alkyl, C$_{1-4}$ alkoxy, NR$_9$C(O)R$_a$, C(O)NR$_6$R$_7$, S(O)$_3$H, or C(O)OC$_{1-4}$ alkyl; and $X_2$ is oxygen or sulfur;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; (CR$_8$R$_8$)q S(O)$_t$R$_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heterocyclic, heterocyclic $C_{1-4}$alkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; (CR$_8$R$_8$)qNR$_4$R$_5$; $C_{2-10}$ alkenyl C(O)NR$_4$R$_5$; (CR$_8$R$_8$)q C(O)NR$_4$R$_5$; (CR$_8$R$_8$)q C(O)NR$_4$R$_{10}$; S(O)$_3$H; S(O)$_3$R$_8$; (CR$_8$R$_8$)q C(O)R$_{11}$; $C_{2-10}$ alkenyl C(O)R$_{11}$; $C_{2-10}$ alkenyl C(O)OR$_{11}$(CR$_8$R$_8$)q C(O)OR$_{12}$; (CR$_8$R$_8$)q OC(O)R$_{11}$; (CR$_8$R$_8$)q NR$_4$C(O)R$_{11}$, (CR$_8$R$_8$)q NHS(O)$_2$R$_{17}$, (CR$_8$R$_8$)q S(O)$_2$NR$_4$R$_5$; or two $R_1$ moieties together may form O—(CH$_2$)$_s$O— or a 5 to 6 membered unsaturated ring;

q is 0, or an integer having a value of 1 to 10;

t is 0, or an integer having a value of 1 or 2;

s is an integer having a value of 1 to 3;

v is 0, or an integer having a value of 1 to 4;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic $C_{1-4}$ alkyl, or $R_4$ and $R_5$ together with the nitrogen to which they are attached form a 5 to 7 member ring which may optionally comprise an additional heteroatom selected from O/N/S;

Y is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; (CR$_8$R$_8$)q S(O)$_t$R$_4$; hydroxy; hydroxyC$_{1-4}$alkyl; aryl; aryl $C_{1-4}$ alkyl; aryloxy; arylC$_{1-4}$ alkyloxy; heteroaryl; heteroarylalkyl; heteroaryl $C_{1-4}$ alkyloxy; heterocyclic, heterocyclic $C_{1-4}$alkyl; aryl $C_{2-10}$ alkenyl; heteroaryl $C_{2-10}$ alkenyl; heterocyclic $C_{2-10}$ alkenyl; (CR$_8$R$_8$)q NR$_4$R$_5$; $C_{2-10}$ alkenyl C(O)NR$_4$R$_5$; (CR$_8$R$_8$)q C(O)NR$_4$R$_5$; (CR$_8$R$_8$)q C(O)NR$_4$R$_{10}$; S(O)$_3$H; S(O)$_3$R$_8$; (CR$_8$R$_8$)q C(O)R$_{11}$; $C_{2-10}$ alkenyl C(O)R$_{11}$; $C_{2-10}$ alkenyl C(O)OR$_{11}$; C(O)R$_{11}$; (CR$_8$R$_8$)q C(O)OR$_{12}$; (CR$_8$R$_8$)q OC(O)R$_{11}$; (CR$_8$R$_8$)q NR$_4$C(O)R$_{11}$, (CR$_8$R$_8$)q NHS(O)$_2$R$_d$, (CR$_8$R$_8$)q S(O)$_2$NR$_4$R$_5$; or two Y moieties together may form O—(CH$_2$)$_s$O— or a 5 to 6 membered unsaturated ring;

$R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur;

n is an integer having a value of 1 to 3;

m is an integer having a value of 1 to 3;

$R_8$ is hydrogen or $C_{1-4}$ alkyl;

$R_{10}$ is $C_{1-10}$ alkyl $C(O)_2R_8$;

$R_{11}$ is hydrogen, $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl;

$R_{12}$ is hydrogen, $C_{1-10}$ alkyl, optionally substituted aryl or optionally substituted arylalkyl;

$R_{13}$ and $R_{14}$ are independently hydrogen, optionally substituted $C_{1-4}$ alkyl, or one of $R_{13}$ and $R_{14}$ may be optionally substituted aryl;

$R_{17}$ is $C_{1-4}$alkyl, aryl, arylalkyl, heteroaryl, heteroaryl$C_{1-4}$ alkyl, heterocyclic, or heterocyclic$C_{1-4}$alkyl, wherein the aryl, heteroaryl and heterocyclic rings may all be optionally substituted;

$R_d$ is $NR_6R_7$, alkyl, aryl$C_{1-4}$alklyl, aryl$C_{2-4}$ alkenyl, heteroaryl, hetroaryl-$C_{1-4}$alkyl, heteroaryl$C_{2-4}$ alkenyl, heterocyclic, heterocyclic$C_{1-4}$ alkyl, wherein the aryl, heteroaryl and heterocyclic rings may all be optionally substituted;

E is optionally selected from

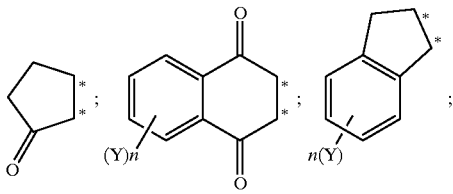

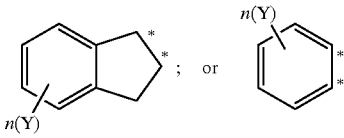

the asterix * denoting point of attachment of the ring; or a pharmaceutically acceptably salt thereof.

10. The compound according to claim 9 wherein the $R_2$ is optionally substituted one to three times by halogen, nitro, halosubstituted $C_{1-10}$ alkyl, $C_{1-10}$ alkyl, $C_{1-10}$ alkoxy, hydroxy, SH, —C(O)$NR_6R_7$, —NH—C(O)$R_a$, —NHS(O)$_2$$R_b$, S(O)$NR_6R_7$, C(O)$OR_8$, or a tetrazolyl ring.

11. The compound according to claim 9 wherein R is OH, —NHS(O)$_2R_b$ or C(O)OH.

12. The compound according to claim 9 wherein $R_1$ is halogen, cyano, nitro, $CF_3$, C(O)$NR_4R_5$, alkenyl C(O)$NR_4R_5$, C(O)$R_4R_{10}$, alkenyl C(O)$OR_{12}$, heteroaryl, heteroarylalkyl, heteroaryl alkenyl, or S(O)$NR_4R_5$.

13. The compound according to claim 9 wherein Y is halogen, $C_{1-4}$ alkoxy, optionally substituted aryl, optionally substituted arylalkoxy, methylene dioxy, $NR_4R_5$, thio$C_{1-4}$ alkyl, thioaryl, halosubstituted alkoxy, optionally substituted $C_{1-4}$alkyl, hydroxy alkyl.

14. The compound according to claim 9 wherein R is OH, SH, or NHS(O)$_2R_b$ and $R_1$ is substituted in the 3-position, the 4-position or di substituted in the 3,4-position by an electron withdrawing moiety.

15. The compound according to claim 9 wherein the A containing ring is a pyridine ring.

16. A pharmaceutical composition comprising an effective amount of a compound according to claim 9 and a pharmaceutically acceptable carrier or diluent.

* * * * *